US006774358B2

United States Patent
Hamill et al.

(10) Patent No.: US 6,774,358 B2
(45) Date of Patent: Aug. 10, 2004

(54) NORMALIZATION APPARATUS FOR PET AND SPECT SCANNERS AND METHOD FOR USING SAME

(75) Inventors: James J. Hamill, Knoxville, TN (US); Michael E. Casey, Knoxville, TN (US); Timothy G. Gremillion, Knoxville, TN (US); Wing K. Luk, Knoxville, TN (US); Stephen Miller, Knoxville, TN (US)

(73) Assignee: CTI Pet Systems, Inc., Knoxville, TN (US)

( * ) Notice: Subject to any disclaimer, the term of this patent is extended or adjusted under 35 U.S.C. 154(b) by 66 days.

(21) Appl. No.: 10/103,276

(22) Filed: Mar. 21, 2002

(65) Prior Publication Data

US 2003/0178559 A1 Sep. 25, 2003

(51) Int. Cl.[7] ................................................. G01K 5/00
(52) U.S. Cl. ............................. 250/252.1; 250/363.03
(58) Field of Search ......................... 250/252.1, 363.03, 250/363.04, 370.07, 370.09, 370.1, 493.1, 494.1, 352.1; 600/427

(56) References Cited

U.S. PATENT DOCUMENTS 5,739,540 A * 4/1998 Motomura et al. .... 250/363.04
6,429,434 B1 * 8/2002 Watson et al. ......... 250/363.04
6,490,476 B1 * 12/2002 Townsend et al. .......... 600/427
2003/0076988 A1 * 4/2003 Liang et al. ................ 382/131

OTHER PUBLICATIONS

Bailey, Dale L. et al., "An Investigation of Factors Affecting Detector and Geometric Correction in Normalization of 3–D PET Data," IEEE Transactions on Nuclear Science, vol. 43, No. 6, pp. 3300–3307, Dec. 1996.

* cited by examiner

Primary Examiner—Constantine Hannaher
Assistant Examiner—Otilia Gabor
(74) Attorney, Agent, or Firm—Pitts & Brittian PC

(57) ABSTRACT

Apparatus and methods for simulating a sheet source with a line source for determining normalization coefficients for the detectors in positron emission tomography (PET) scanners and single photon emission computed tomography (SPECT) scanners. A line source, oriented perpendicular to the axis of a scanner gantry, is moved along the axis while the detectors are stationary and positioned substantially parallel to the plane in which the source moves. In another embodiment, an axially mounted line source moves parallel to a diameter of the gantry while the stationary detectors are positioned substantially parallel to the plane in which the source moves. In still another embodiment, the line source is stationary and positioned parallel to the gantry axis and off center while the detectors move relative to the line source. A shaped attenuator is placed around the source in this last embodiment.

23 Claims, 3 Drawing Sheets

NORMALIZATION APPARATUS FOR PET AND SPECT SCANNERS AND METHOD FOR USING SAME

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to positron emission tomography (PET) and single photon emission computed tomography (SPECT) scanners. More particularly, this invention pertains to apparatus and methods for simulating a sheet source with a line source for determining normalization coefficients for the scanner detectors.

2. Description of the Related Art

Various techniques are used for medical imaging. Positron emission tomography (PET) and single photon emission computed tomography (SPECT) are popular in radiology because of their ability to non-invasively study physiological processes and structures within the body.

Positron Emission Tomography is a nuclear imaging technique used in the medical field to assist in the diagnosis of diseases. PET allows the physician to examine the whole patient at once by producing pictures of many functions of the human body unobtainable by other imaging techniques. In this regard, PET displays images of how the body works (physiology or function) instead of simply how it looks. PET is considered the most sensitive, and exhibits the greatest quantification accuracy, of any nuclear medicine imaging instrument available at the present time. Applications requiring this sensitivity and accuracy include those in the fields of oncology, cardiology, and neurology.

In PET, short-lived positron-emitting isotopes, referred to as radiopharmaceuticals, are injected into a patient. When these radioactive drugs are administered to a patient, they distribute within the body according to the physiologic pathways associated with their stable counterparts. As the radiopharmaceutical isotopes decay in the body, they discharge positively charged particles called positrons. Upon discharge, the positrons encounter electrons, and both are annihilated. As a result of each annihilation event, gamma rays are generated in the form of a pair of diametrically opposed photons approximately 180 degrees (angular) apart. After the PET scanner detects these annihilation "event pairs" over a period of time, the isotope distribution in a cross section of the body is reconstructed. These events are mapped within the patient's body, thus allowing for the quantitative measurement of metabolic, biochemical, and functional activity in living tissue. More specifically, PET images (often in conjunction with an assumed physiologic model) are used to evaluate a variety of physiologic parameters such as glucose metabolic rate, cerebral blood flow, tissue viability, oxygen metabolism, and in vivo brain neuron activity.

Mechanically, a PET scanner consists of a bed, or gurney, and a gantry supporting the tomograph detectors. In some tomographs, the gantry is inside an enclosure having a tunnel through its center, through which the bed traverses. In other tomographs, the detectors are cantilevered over the front of the gantry. In all types of tomographs, the gantry defines a tunnel through which the patient travels. The patient, who has been treated with a radiopharmaceutical, lies on the bed and is moved longitudinally past the detectors. There are four classes of PET tomographs, based on the arrangement of the detectors. Fixed ring scanners have numerous small detectors organized in detector blocks, which are grouped into buckets, and arranged in an arc around the circumference of the gantry. A second class of PET tomographs includes fixed polygonal arrangements of panel detectors. A third class includes detectors arranged in an arc around the circumference of the gantry, with the detectors rotating about the axis of the gantry. A fourth class includes polygonal arrangements of panel detectors, with the panel detectors rotating about the axis of the gantry.

Another known tomography system is single photon emission computed tomography (SPECT). Like PET, SPECT is used to produce an image of organ functions by measuring radiation emitted from a radiopharmaceutical that is inside a patient. However, unlike PET, which detects photon pairs, SPECT detects single photons emitted by the radiopharmaceutical isotope decay. Gamma cameras are used to detect the emitted photons. These gamma cameras typically revolve about a patient, and include collimators and photon-sensitive detectors. The radiopharmaceuticals typically used include Technetium-99 and Thallium-201.

Both PET and SPECT are designed to measure the amount of radioactivity along many lines of response (LOR) that pass through the patient and are intercepted by the scanner's detectors. Measurement errors are always present, and in many cases must be corrected by the software that processes the measurements. In particular, the response measured on each LOR is subject to an error in magnitude. Normalization coefficients represent the relationship between the measured and actual magnitude of radiation and are used to correct the magnitude errors. Normalization coefficients are determined by measuring the difference in sensitivity or efficiency of the detectors in the scanners. Normalization of scanner data is usually performed by estimating the sensitivity or efficiency of a LOR.

"An Investigation of Factors Affecting Detector and Geometric Correction in Normalization of 3-D PET Data," by Dale L. Bailey, David W. Townsend, Paul E. Kinahan, Sylke Grootoonk, and Terry Jones, IEEE Transactions on Nuclear Science, Vol. 43, No. 6, pp. 3300–07, December 1996, describes an apparatus for moving a line source to simulate a plane source for determining normalization coefficients in a PET scanner. The apparatus is an aluminum support carriage with a dc motor driven worm drive that moves the line source along the longitudinal axis of the patient tunnel.

BRIEF SUMMARY OF THE INVENTION

Apparatus and methods for simulating a sheet or planar source with a line source for determining normalization coefficients for PET or SPECT scanner detectors are disclosed. According to one embodiment of the present invention, a line source, oriented parallel to the axis of the patient tunnel, is moved along a diameter of the tunnel. In another embodiment, a line source, oriented perpendicular to the patient tunnel, is moved along the axis of the patient tunnel. These two embodiments simulate a sheet source with a line source fixed to the patient bed, and the bed moving the line source within the patient tunnel of a scanner and the scanner detectors in a stationary, fixed position.

In still another embodiment, an annular sheet source is simulated with a stationary line source, oriented parallel to the axis of the tunnel and offset from the center of the tunnel, with a set of detectors rotating about the tunnel axis in a PET or SPECT scanner. Alternatively, the line source is rotated about the axis of a set of stationary detectors mounted on a fixed ring or gantry. In either case, the detectors see an annular sheet source, and a sinogram is generated. In another embodiment, a shaped attenuator surrounds the line source to ensure each detector receives equal flux levels of radiation because, with the line source offset from the center axis, the line source is positioned nearer one detector than its opposite member. The shaped attenuator increases the scattered radiation from the line source. For other embodiments, an attenuating medium is used to increase the scattered radiation.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Apparatus and methods for simulating a sheet source with a line source for determining normalization coefficients for PET and SPECT scanner detectors are disclosed. A line source, with a specified orientation with respect to the scanner detectors, is used to simulate a planar or sheet source. The detectors in the scanner produce a sinogram of the simulated sheet source and normalization coefficients are determined from the sinogram.

Figure 1:
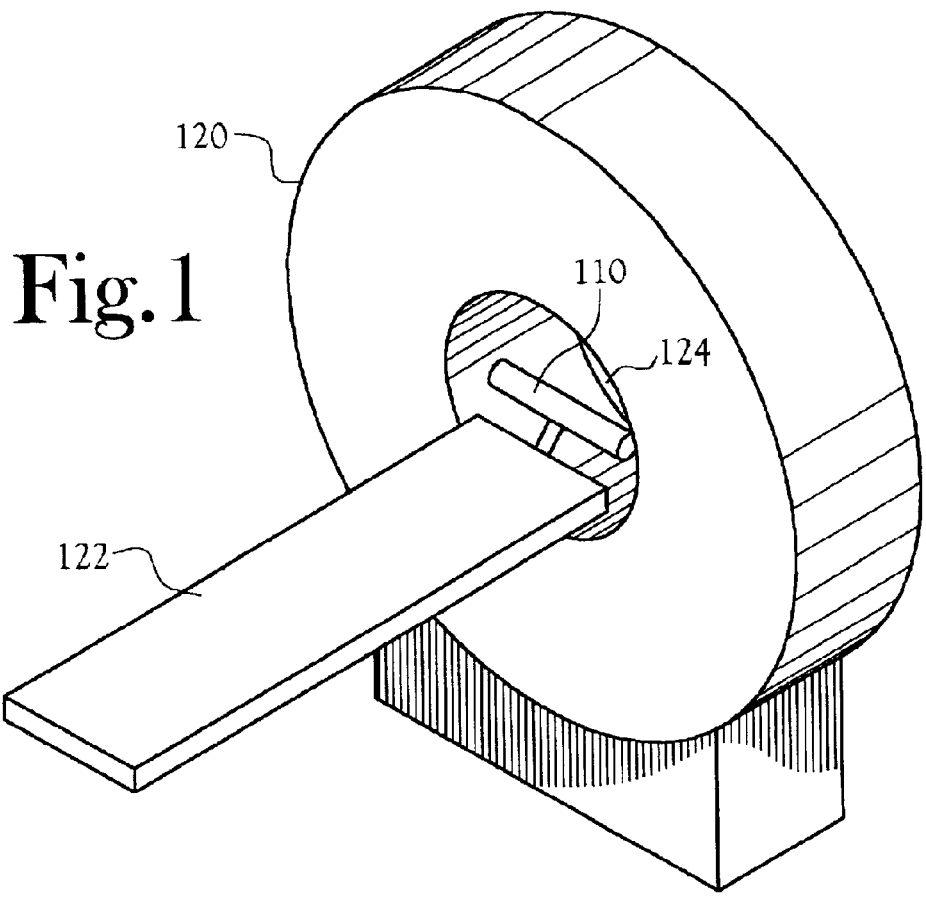
FIG. 1 is a perspective view of a PET or SPECT scanner showing a patient bed with a horizontally oriented source.
Figure 2:
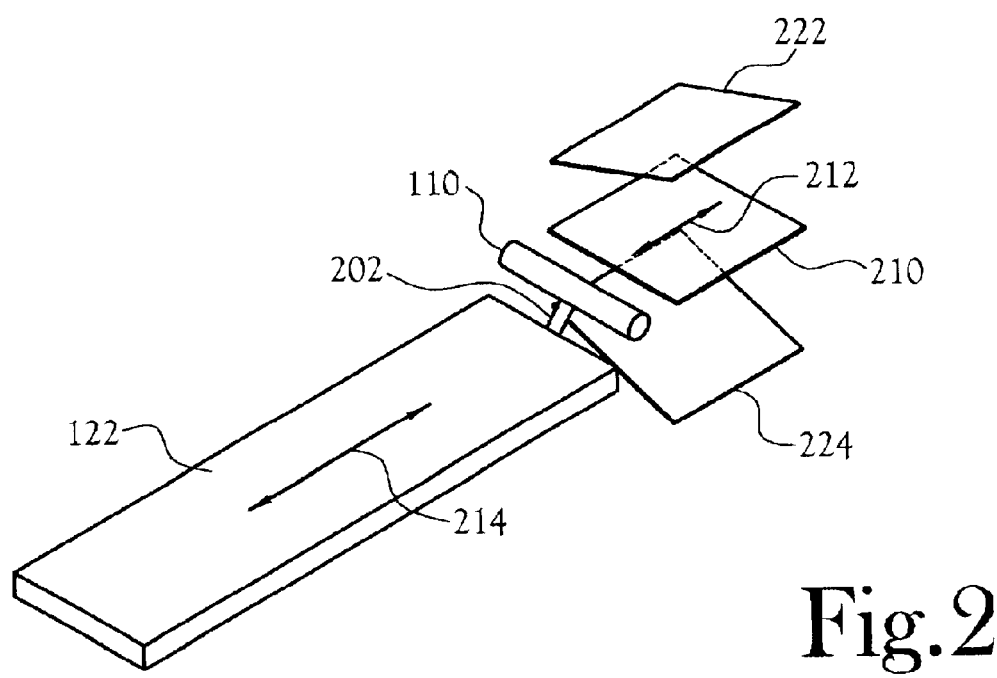
FIG. 2 is a pictorial showing the scanner bed, the plane of the detectors, and a horizontally oriented source.

FIG. 1 illustrates an embodiment of the invention using a line source 110 oriented perpendicular to the axis of the patient tunnel 124, which simulates a horizontally oriented planar source 210, shown in FIG. 2. The patient tunnel 124 is defined by the tomograph gantry, on which the detectors are attached. Those skilled in the art will recognize that this arrangement can be used with either a PET or a SPECT scanner without departing from the spirit and scope of the present invention.

A line source 110 is attached to a patient bed 122 of either a PET or SPECT scanner 120. The line source 110 is positioned above the surface of the bed 122 and in front of the bed 122, resulting in the source 110 being positioned horizontally in the scanner tunnel 124 and without having the bed 122 attenuating the radiation from the source 110.

FIG. 2 illustrates the relationship of the scanner detectors 222 and 224 to a simulated plane source 210 produced by the horizontal line source 110. The scanner 120 has detectors attached to a gantry in a configuration dependant upon the class of tomograph. Fixed ring PET scanners have numerous small detectors organized in detector blocks, which are grouped into buckets, and arranged in an arc around the circumference of the gantry. Fixed polygonal PET scanners have polygonal arrangements of panel detectors. Rotating ring PET scanners have detectors arranged in an arc around the circumference of the gantry, with the detectors rotating about the axis of the gantry, and rotating polygonal ring PET scanners have polygonal arrangements of panel detectors rotating about the axis of the gantry. The detectors 222, 224, which can be one or more detector blocks or panels, are illustrated in FIG. 2 as planar panels positioned above and below the simulated plane source 210. In the illustrated embodiment, the line source 110 simulates a plane source 210 when the bed 122 moves in a longitudinal direction 214. As the bed 122 moves, the line source 110 follows a path 212, simulating a plane source 210. The source plane 210 is substantially parallel to the planes of the detectors 222, 224. Those skilled in the art will recognize that the planes of the detectors 222, 224 can be parallel or at an acute angle to each other, depending upon the configuration of the detectors in the scanner 120 and whether the scanner 120 is a PET or SPECT scanner.

With the line source 110 in a substantially central position vertically in the scanner opening 124, the line source 110 is located at approximately the same distance from the detectors 222 and 224, resulting in similar count rates at the detectors 222 and 224. The illustrated embodiment shows a mounting arm 202 securing the source 110 to the bed 122, with the source 110 positioned in front of the bed 122 such that the bed 122 does not attenuate the detected radiation from the source 110. Those skilled in the art will recognize that the line source 110 can be mounted on the bed in various ways without departing from the spirit and scope of the present invention. In the illustrated embodiment, the built-in drive system for the bed 122 moves the bed 122 along a longitudinal axial path 214 and the attached line source 110 along the planar path 212 at the desired speed. Although the line source 110 is illustrated in FIG. 2 with a horizontal orientation, the mounting arm 202 permits the line source 110 to be rotated to the desired orientation.

As the patient bed 122 moves horizontally into the scanner tunnel 124, the line source 110 traverses a horizontal planar path 210. The detectors 222 and 224 are held stationary in a fixed position and acquire a sinogram during the time the line source 110 traverses the planar path 210, resulting in the same sinogram that would be acquired from a sheet source. The sinogram is acquired at a fixed orientation of the scanner detectors 222 and 224. Fixed angle normalization coefficients are directly determined from the sinogram, and normalization coefficients are determined for other angles. In one embodiment, the patient bed 122, and consequently, the line source 110, move at a uniform speed. Those skilled in the art will recognize that the line source 110 can be at another orientation other than horizontal, provided that the spatial relationship between the line source 110 and the detectors 222 and 224 is maintained, without departing from the spirit and scope of the present invention.

Figure 3:
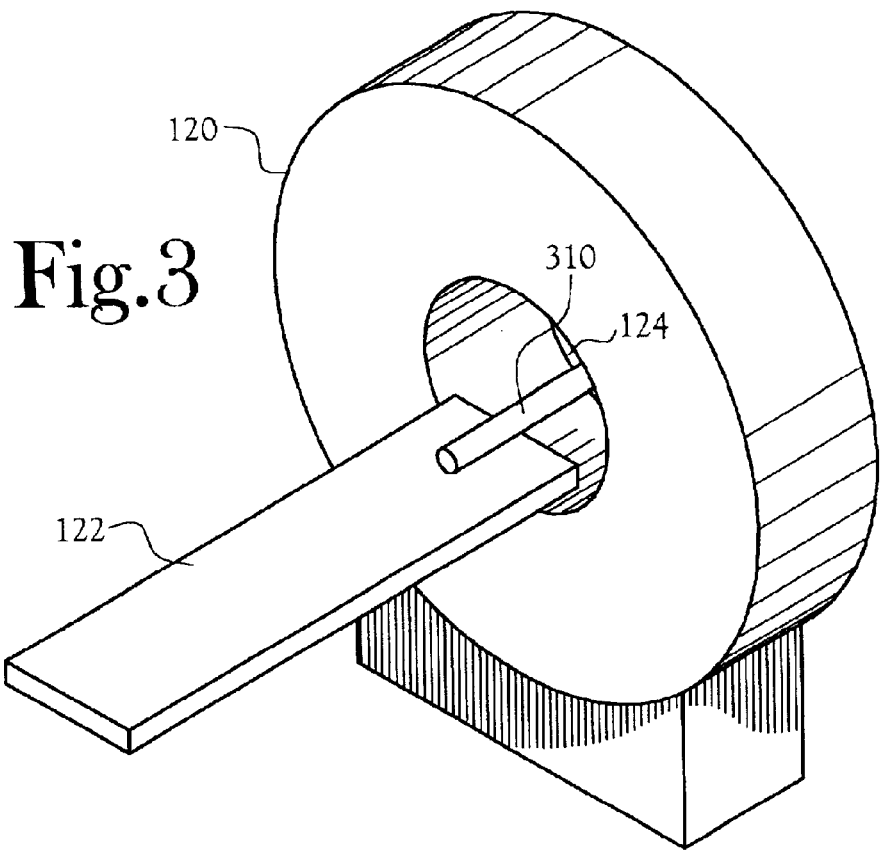
FIG. 3 is a perspective view of PET or SPECT scanner showing a patient bed with an axially oriented source.
Figure 4:
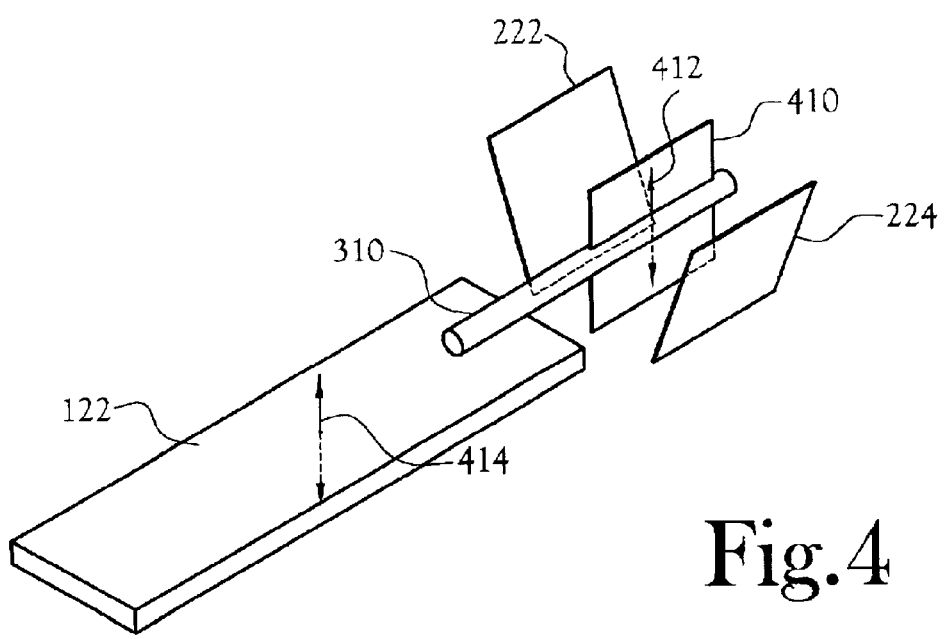
FIG. 4 is a pictorial showing the scanner bed, the plane of the detectors, and an axially oriented source.

FIG. 3 illustrates an embodiment of the invention using an axially oriented line source 310, which simulates a vertically oriented planar source 410, shown in FIG. 4. Those skilled in the art will recognize that this arrangement can be used with either a PET or a SPECT scanner without departing from the spirit and scope of the present invention.

A line source 310 is attached to a patient bed 122 of either a PET or SPECT scanner 120. The line source 310 is illustrated positioned above the surface of the bed 122 and extending into the scanner tunnel 124 such that the line source 310 is parallel to the axis formed by the patient tunnel 124 and positioned horizontally in the tunnel 124. Those skilled in the art will recognize that the relative position of the line source 310 to the bed 122 can be changed without departing from the spirit and scope of the present invention.

FIG. 4 illustrates the relationship of the detectors 222 and 224 to the simulated source plane 410 of the horizontal line source 310. The detectors 222, 224, which can be one or more detector blocks or panels, are illustrated in FIG. 4 as planar panels positioned on either side of the simulated plane source 410. In the illustrated embodiment, the bed 122 moves in a vertical direction 414, and the line source 310 follows a path 412 illustrated as a plane source 410. The plane source 410 is substantially parallel to the planes of the detectors 222, 224. Those skilled in the art will recognize that the planes of the detectors 222, 224 can be parallel or at an acute angle to each other, depending upon the configuration of the detectors in the scanner 120 and whether the scanner 120 is a PET or SPECT scanner.

The line source 310 is located in a substantially central position horizontally between the side walls of the scanner tunnel 124, such that the source 310 is at approximately the same distance from the detectors 222 and 224, resulting in similar count rates at the detectors 222 and 224. The active portion of the line source 310 extends past the patient bed 122 such that the bed 122 does not attenuate the radiation from the source 310 and detected by the detectors 222 and 224. In the illustrated embodiment, the line source 310 is as long as or longer than the axial length of the detectors 222 and 224, and the line source 310 is positioned axially such that the midpoint of its length is substantially at the midpoint of the axial length of the detectors 222 and 224. Those skilled in the art will recognize that a line source 310 with a shorter length can be used to determine normalization coefficients of less than all of the detector assembly without departing from the spirit and scope of the present invention.

The illustrated embodiment does not show the attachment of the line source 310 to the patient bed 122. Those skilled in the art will recognize that various means for attaching the source 310 can be used without departing from the spirit and scope of the present invention. Also, those skilled in the art will recognize that other means for moving the line source 310 can be used without departing from the spirit and scope of the present invention. For example, the line source 310 is held in position and moved vertically by an assembly not dependent upon the patient bed 122 for the vertical motion. In another embodiment, the axial line source 310 is moved along a line defining a diameter of the tunnel 124 with the detectors 222 and 224 positioned substantially parallel to the diameter line, such that the spatial relationship between the line source 310 and the detectors 222 and 224 is maintained.

As the patient bed 122 moves vertically, the line source 310 traverses a vertical planar path 410. The scanner detectors 222 and 224 are held stationary in a fixed position and acquire a sinogram during the time the line source 310 traverses the planar path 410. The resulting sinogram is identical to the sinogram that would be acquired from a sheet source. The sinogram is acquired at a fixed orientation of the scanner detectors 222 and 224. Fixed angle normalization coefficients are directly determined from the sinogram, and normalization coefficients are determined for other angles. In the illustrated embodiment, the built-in drive system for the bed 122 moves the bed 122 along a vertical path 414 and the attached line source 310 along the planar path 412 at the desired speed. In one embodiment, the patient bed 122, and consequently, the line source 310, moves at a uniform speed.

In the embodiment illustrated in FIGS. 3 and 4, if the source 310 is held in a cylindrical source container thick enough to stop positrons emitted by germanium-68, the source container is also thick enough to attenuate the annihilation radiation. The attenuation factor due to the thickness of the line source 310 container is constant for all LORs that comprise a segment of the three-dimensional sinogram.

Figure 5:
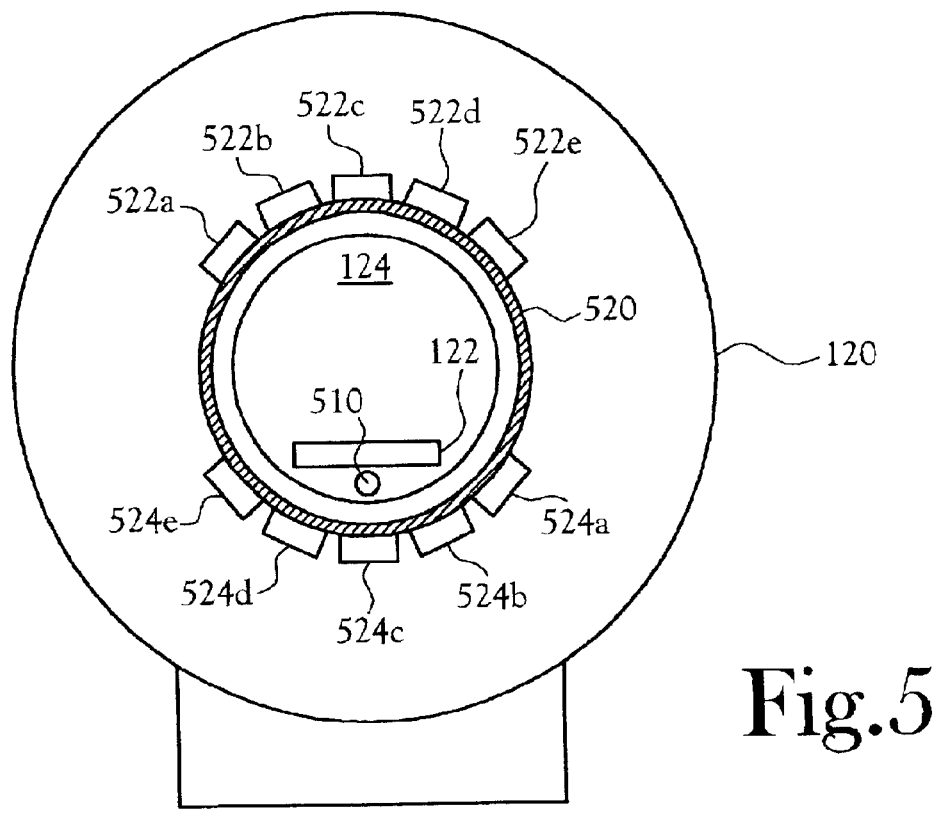
FIG. 5 is a section view of a scanner showing the gantry with detectors and an axially oriented line source.
Figure 6:
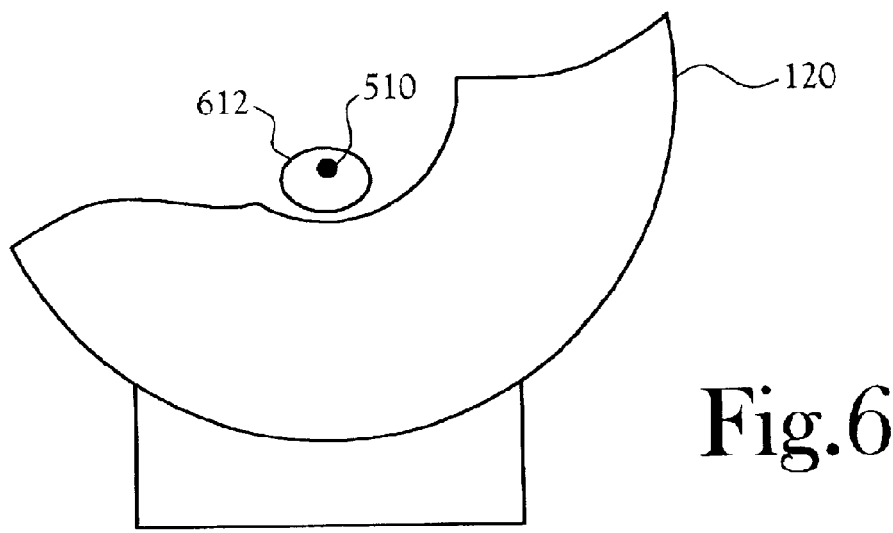
FIG. 6 shows a partial front view of a simulated annular sheet source with a shaped attenuator.

FIG. 5 illustrates an embodiment of the invention using an axially oriented line source 510 and a fixed ring of detectors 522, 524. This line source 510 is located off-center from the axis of the tunnel 124 and simulates an annular sheet source. FIG. 6 is a partial front view of a tomography scanner 120 showing the source 610 surrounded by an attenuator 612. Those skilled in the art will recognize that this arrangement can be used with either a PET or a SPECT scanner without departing from the spirit and scope of the present invention.

A line source 510 is positioned axially in the patient tunnel 124 of either a PET or SPECT scanner 120. The line source is positioned off-center to the axis of the tunnel 124 and close to the inside surface of the tunnel 124. The configuration of this embodiment is similar to that shown in FIGS. 3 and 4; however, in one embodiment, the line source 510 is held stationary while the detectors 522 and 524, mounted on a gantry 520, rotate about a longitudinal axis of the tunnel 124. By virtue of the rotation, the line source 510 simulates an annular sheet source. While the detectors 522 and 524 rotate and the line source 510 is held stationary, the detectors 522 and 524 acquire a sinogram, resulting in the same sinogram that would be acquired from an annular sheet source. This embodiment is suitable for tomographs with detectors that rotate about the axis of the gantry. In another embodiment, the line source 510 is rotated about the axis of the tunnel 124 with the detectors 522 and 524 held stationary. This embodiment is suitable for tomographs with fixed detectors and for tomographs with detectors that rotate about the axis of the gantry.

In one embodiment, the line source 510 is affixed to the patient bed 122, with the line source 510 extending past the end of the bed 122 and with the bed not extending into the tunnel 124 such that the bed 122 does not cross the first direct plane of the first detector 522 or 524, or pair of detectors 522 and 524, to be normalized. The illustrated embodiment does not show the attachment of the line source 510 in the tunnel 124. Those skilled in the art will recognize that various means for attaching the source 510 inside the tunnel 124 can be used without departing from the spirit and scope of the present invention.

FIG. 6 illustrates another embodiment in which a shaped attenuator 612 surrounds a line source 510. This embodiment is used in an arrangement similar to that illustrated in FIG. 5.

Without a shaped attenuator 612, the detectors nearest the line source 510 receive a higher radiation flux than the detectors further away from the line source 510. A shaped attenuator 612 places a larger amount of attenuating material between the line source 510 and the nearer detectors than between the line source 510 and the further detectors. The shape, and consequently the attenuation factor, is mathematically chosen such that the total path length, that is, the sum of the path lengths of the two quanta emitted in opposite directions, takes on the same value at all angles. To accomplish this, the shaped attenuator 612 maintains a fixed orientation towards the axial center of the tunnel 124. That is, as the line source 510 follows a cylindrical path about the center axis of the tunnel 124, the shaped attenuator 612 rotates about the line source 510 such that a point on the surface of the attenuator 612 is fixed relative to the center axis of the tunnel 214.

The form of a shaped attenuator is defined by the following polar-coordinate equation:

$$r(\theta) = C + \sum_{odd\ k} a_k \cdot \cos k\theta$$

where
- θ=angle in radians, the angle being 0 in the direction of the tomograph's central axis
- C=constant
- k=constant
- a=radial parameter A simple shaped attenuator 612, as illustrated in FIG. 6, has a form defined by the equation:

$$r(\theta) = C - a \cdot \cos \theta$$

where
- θ=angle in radians
- C=constant
- a=radial parameter

In the illustrated embodiments, the amount of scattered radiation is increased by surrounding the line source 110, 310, 510 in an attenuating medium. For example, a hollow tube of lead, steel, or aluminum can be used, in which case, the line source 110, 310, 510 is held in the middle of the hollow tube. Scattering the radiation from the line source 110, 310, 510, improves the normalization coefficients. The shaped attenuator 612 also provides scattered radiation.

The embodiment illustrated in FIG. 5 shows five detector pairs in the scanner. Each set of five detectors is arranged in a head, and two heads 522 and 524 are illustrated. Those skilled in the art will recognize that any number of detectors and any number of heads can be used without departing from the spirit and scope of the present invention.

From the foregoing description, it will be recognized by those skilled in the art that apparatus for simulating a sheet source with a line source for determining normalization coefficients for PET and SPECT scanners and methods for using the apparatus have been provided. A line source simulates a sheet, or planar, source, and the simulated source is either flat and planar or annular.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. An apparatus for simulating a sheet source for determining normalization coefficients, said apparatus comprising:
   a tomography scanner having a gantry, said gantry having an axis; said tomography scanner having at least one detector attached to said gantry;
   a patient bed adapted to move relative to said gantry of said scanner; and
   a line source attached to said patient bed, said line source adapted to fit into a tunnel defined by said gantry.

2. The apparatus of claim 1 wherein said line source is positioned substantially perpendicular to said axis of said gantry, and said patient bed moves said line source in a longitudinal direction parallel to said axis of said gantry.

3. The apparatus of claim 1 wherein said line source is positioned substantially parallel to said axis of said gantry, and said patient bed moves said line source in a direction parallel to a diameter of said gantry.

4. The apparatus of claim 1 further including an attenuator enclosing said line source.

5. The apparatus of claim 1 wherein said patient bed moves said line source at a uniform speed.

6. The apparatus of claim 1 wherein said line source is positioned substantially parallel and off center to said axis of said gantry, and said patient bed fixes said line source in a stationary position about said axis at a specified radius, whereby said gantry rotates about said axis.

7. The apparatus of claim 6 wherein said line source is enclosed in an attenuator.

8. The apparatus of claim 7 wherein said attenuator is a shaped attenuator.

9. The apparatus of claim 7 wherein said attenuator includes a means for radially varying a radiation flux emitted from said line source.

10. The apparatus of claim 7 wherein said attenuator radially varies a radiation flux emitted from said line source, and said at least one detector includes a first detector and a second detector, wherein said radiation flux has a lesser value in the direction of a closer one of said first detector and said second detector.

11. The apparatus of claim 1 further including a device for acquiring a sinogram from radiation emitted by said line source, whereby a plurality of normalization coefficients are determined from said sinogram.

12. An apparatus for simulating a sheet source for determining normalization coefficients, said apparatus comprising:
   a tomography scanner having a gantry, said gantry having an axis; said tomography scanner having at least one detector;
   a line source positioned substantially parallel to said axis, said line source positioned off-center relative to said axis; and
   a moving device causing said line source to revolve about said axis at a specified radius, said line source moving relative to said at least one detector for determining normalization coefficients.

13. The apparatus of claim 12 wherein said line source is enclosed in an attenuator.

14. The apparatus of claim 12 wherein said line source is enclosed in a shaped attenuator, said shaped attenuator rotating such that said shaped attenuator maintains a fixed relationship with respect to said axis.

15. The apparatus of claim 12 further including a device for acquiring a sinogram from radiation emitted by said line source, whereby a plurality of normalization coefficients are determined from said sinogram.

16. A method for determining normalization coefficients, said method comprising the steps of:
   (a) positioning a line source in a tunnel defined by a gantry of a tomography scanner, said tunnel having an axis; said tomography scanner having at least one detector;
   (b) changing the spatial relationship between said line source and said at least one detector;
   (c) acquiring a sinogram; and
   (d) determining normalization coefficients from said sinogram.

17. The method of claim 16 wherein said line source is surrounded by an attenuator.

18. The method of claim 16 wherein said step of positioning said line source includes a step of positioning said line source substantially perpendicular to said axis of said tunnel; and wherein said step of changing said spatial relationship includes the steps of positioning said line source substantially parallel to a plane defined by said at least one detector, attaching said line source to a patient bed, and moving said patient bed such that said line source moves along said axis of said tunnel.

19. The method of claim 16 wherein said step of positioning said line source includes a step of positioning said line source substantially parallel to the axis of said tunnel; and wherein said step of changing said spatial relationship includes a step of positioning said at least one detector in a fixed position and a step of causing said line source to move in a path substantially parallel to a plane defined by said at least one detector.

20. The method of claim 16 wherein said step of positioning said line source includes a step of positioning said line source substantially parallel to the axis of said tunnel; and wherein said step of changing said spatial relationship includes a step of positioning said at least one detector and a step of causing said line source to move along a diameter of said tunnel.

21. The method of claim 16 wherein said step of positioning said line source includes a step of positioning said line source substantially parallel to said axis of said tunnel and closer to a surface of said tunnel than to a diametrically opposite surface of said tunnel; and wherein said step of changing said spatial relationship includes a step of fixedly positioning said line source and a step of rotating said at least one detector around said axis.

22. The method of claim 21 wherein said step of positioning said line source includes a step of surrounding said line source with a shaped attenuator.

23. The method of claim 16 wherein said step of changing the spatial relationship includes moving said line source at a uniform speed.

* * * * *